United States Patent [19]
Chappell et al.

[11] Patent Number: 6,002,071
[45] Date of Patent: Dec. 14, 1999

[54] TRANSCRIPTIONAL SILENCING ELEMENTS AND THEIR BINDING FACTORS

[75] Inventors: Joseph Chappell, Lexington, Ky.; Jeffrey D. Newman, Williamsport, Pa.; Shaohui Yin, Ardmore, Okla.

[73] Assignee: University of Kentucky, Lexington, Ky.

[21] Appl. No.: 08/874,563

[22] Filed: Jun. 13, 1997

Related U.S. Application Data

[60] Provisional application No. 60/020,087, Jun. 13, 1996.

[51] Int. Cl.$^6$ .............................. A01H 5/00; A01H 5/10; C07H 21/04; C12N 5/14; C12N 15/82
[52] U.S. Cl. ....................... 800/298; 435/320.1; 435/419; 536/24.1; 800/278
[58] Field of Search .............................. 435/172.3, 302.1, 435/419; 800/205, 278, 298; 536/24.1

[56] References Cited

PUBLICATIONS

Harrison et al., "Stress responses in alfalfa (*Medicago sativa* L.). 8. Cis–elements and trans–acting factors for the quantitative expression of a bean chalcone synthase gene promoter in electroporated alfalfa protoplasts" Plant Mol. Biol. 16:877–890 (1991).

Lawton et al., "Silencer region of chalcone synthase promoter contains multiple binding sites for a factor, SBF–1, closely related to GT–1" Plant Mol. Biol. 16:235–249 (1991).

Harrison et al. "Characterization of a nuclear protein that binds to three elements within the silencer region of a bean chalcone synthase gene promoter" Proc. Natl. Acad. Sci. USA 88:2515–2519 (1991).

Loake et al., "Combination of H–box [CCTACC(N)7CT] and G–box (CACGTG) cis celements is necessary for feed-–forward stimulation of a chalcone synthase promoter by the phenylpropanoid–pathway intermediate p–coumaric acid" Proc. Natl. Acad. Sci. USA 89:9230–9234 (1992).

Yu et al., "Purification and biochemical characterization of proteins which bind to the H–box cis–element implicated in transcriptional activation of plant defense genes" Plant Journal 3:805–816 (1993).

Staiger et al., "Purification of tobacco nuclear proteins binding to a CACGTG motif of the chalcone synthase promoter by DNA affinity chromatography" Eur. J. Biochem, 199: 519–527 (1991).

Staiger et al., "A CACGTG motif of the Antirrhinum majus chalcone synthase promoter is recognized by an evolutionarily conserved nuclear protein" Proc. Natl. Acad. Sci. USA 86: 6930–6934 (1989).

Oeda et al., "A tobacco bZip transcription activator (TAF–1) binds to a G–box–like motif conserved in plant genes" EMBO J. 10:1793–1802 (1991).

Schindler et al., "Heterodimerization between light–regulated and ubiquitously expressed arabidopsis GBF bZIP proteins" EMBO J. 11:1261–1273 (1992).

Kim et al., "Identification of G–box sequence as an essential element for methyl jasmonate response of potato proteinase inhibitor II Promoter" Plant Physiol. 99:627–631 (1992).

Fukuda and Shinshi, "Characterization of a novel cis–acting element that is responsive to a fungal elicitor in the promoter of a tobacco class chitinase gene" Plant Mol. Biol. 24:485–493 (1994).

Matton et al., "Identification of cis–acting elements involved in the regulation of the pathogenesis–related gene STH–2 in potato" Plant Mol. Biol. 22:279–291 (1993).

Despres et al., "The activation of the potato PR–10a gene requires the phosphorylation of the nuclear factor PBF–1" Plant Cell 7:589–598 (1995).

Meller et al., "DNA–protein interactions on a cis–DNA element essential for ethylene regulation" Plant Mol. Biol. 23:453–463 (1993).

Threlfall and Whitehead, "Co–ordinated inhibition of squalene synthetase and induction of enzymes of sesquiterpene phytoalexin biosynthesis in cultures of *Nicotiana Tabacum*" Phytochemistry 27:2567–2580 (1988).

Vogeli and Chappell, "Indiction of sesquiterpene cyclase and suppression of squalene synthetase activities in plant cell cultures treated with fungal elicitor" Plant Physiol. 88:1291–1296 (1988).

Zook and Kuc, "Induction of sesquiterpene cyclase and suppression of squalene synthetase activity in elicitor-–treated or fungal–infected potato tuber tissue" Physiol. Mol. Plant Pathol. 39:377–390 (1991).

Whitehead et al., "5–epi–aristolochene is a common precursor of the sesquitepernoid phytoalexins capsidiol and debneyol" Phytochemistry 28:775–779 (1989).

Vogeli et al., "Purification and characterization of an inducible sesquitepene cyclase from elicitor–treated tobacco cell suspension cultures" Plant Physiol. 93:182–187 (1990).

Vogeli and Chappel, "Regulation of a sesquiterpene cyclase in cellulase–treated tobacco cell suspension cultures" Plant Physiol. 94: 1860–1866 (1990).

Facchini and Chappell, "Gene family for an elicitor–induced sesquiterpene cyclase in tobacco" Proc. Natl. Acad. Sci. USA 89: 11088–11092 (1992).

Back et al., "Expression of a plant sesquiterpene cyclase gene in *Escherichia coli*" Arch. Biochem. Biophys. 315:527–532 (1994).

Bowler and Chua, "Emerging themes of plant signal transduction" Plant Cell 6:1529–1541 (1994).

(List continued on next page.)

*Primary Examiner*—Lynette R. F. Smith
*Assistant Examiner*—Amy J. Nelson
*Attorney, Agent, or Firm*—Clark & Elbing LLP

[57] ABSTRACT

The invention features an isolated gene silencing regulatory element that includes 5' TACNNTAC 3'. Vectors, transgenic plants and seeds thereof that include such a gene silencing regulatory element are also disclosed. The invention further provides methods of decreasing the transcription of a DNA sequence in a transgenic plant using the isolated gene silencing regulatory element.

19 Claims, 11 Drawing Sheets

OTHER PUBLICATIONS

Back and Chappell, "Identifying functional domains with terpene cyclases using a domain–swapping strategy" Proc. Natl. Acad. Sci. USA 93:6841–6845 (1996).

Chappell and Nable, "Induction of Sesquiterpenoid Biosynthesis in Tobacco Cell Suspension Cultures by Fungal Elicitor" Plant Physiol. 85: 469–473 (1987).

Lawton et al. Silencer region of a chalcone synthase promoter contains multiple binding sites for a factor, SBF–1, closely related to GT–1. Plant Molecular Biology, 16:235–249, 1991.

Harrison et al. Characterizationof a nuclear protein that binds to three elements within the silencer region of a bean chalcone synthase gene promoter. PNAS USA. 88:2515–1519, Mar. 1991.

Chye et al. Three genes encode 3–hydroxy–3–methylgultaryl–coenzyme A reductase in *Hevea brasiliensis*: hmg1 and hmg3 are differentially expressed. Plant Molecular Biology. 19:473–484, 1992.

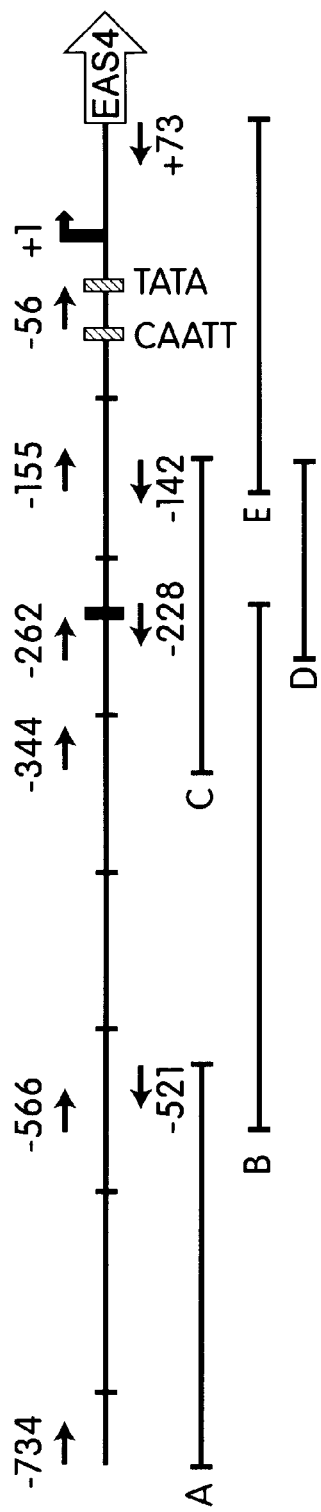
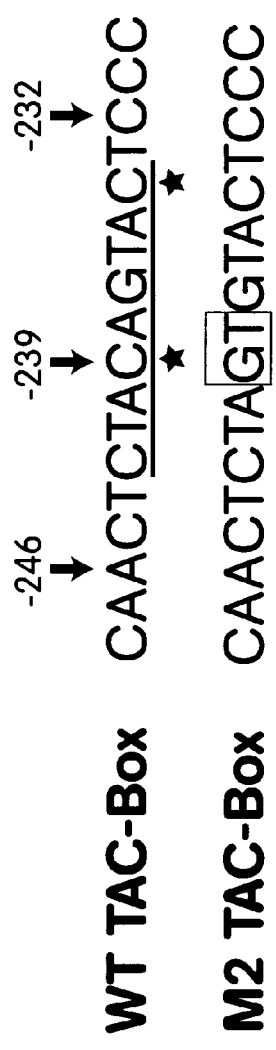
Fig. 1A
Fig. 2B

```
                        SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: Genomic DNA (xi) SEQUENCE DESCRIPTION: SEQ ID NO:1:

NTACNNTACN                                                                10

(2) INFORMATION FOR SEQ ID NO:2:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: Genomic DNA (xi) SEQUENCE DESCRIPTION: SEQ ID NO:2:

CTACAGTACT                                                                10

(2) INFORMATION FOR SEQ ID NO:3:

(i) SEQUENCE CHARACTERISTICS:
         (A) LENGTH: 11 base pairs
         (B) TYPE: nucleic acid
         (C) STRANDEDNESS: single
         (D) TOPOLOGY: linear (ii) MOLECULE TYPE: Genomic DNA (xi) SEQUENCE DESCRIPTION: SEQ ID NO:3:

TCTACAGTAC T                                                              11

(2) INFORMATION FOR SEQ ID NO:4:
```

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:4:

ACTCTACAGT ACTC                                                            14

(2) INFORMATION FOR SEQ ID NO:5:

(i) SEQUENCE CHARACTERISTICS:
        (A) LENGTH: 1368 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:5:

AAGCTTTACG AATTAGATGT AAAAAGACAC AAACTACTTA TATATATTAC CAAAGTAACT           60

TGAAAGTTTA AAATTTCAAT TAGAACTATA GTAGGGTAAA ACTGTCTATT TAAAATCAGT          120

ATTTAAAAAG GCATGAGCGA AAGATGAGGC GTTTTATCTA ACACGAAGCG AGGTGTAAGC          180

CCCATGGTGT TTTATTTTTA TATTTTATAA ATTTATAAAA TCATTATATA AATCAGAAAA          240

ATACACTAAA ATTGTGAAAA GTTAAAGAAA ATTATAGAAT TAATATATAT ATATATATAT          300

ATATATATAT ATATATATAT ATATATATAT ATATATATAA ATGTATGTGT GTGTGTGTGT          360

GTATCGCATG CGCGCGACCA TGCAACTTTT TTTTCTTGAA AAAATAAAAG GCGTAAAGAT          420

ACATTATACC TATGTCATCA AAACAATATA ATATATATAT ATATATATAT ATATATATAT          480

ATATATATAA ATGTATGTGT GTGTGTGTGT GTATCGCATG CGCGCGACCA TGCAACTTTT          540

TTTTCTTGAA AAAATAAAAG GCGTAAAGAT ACATTATACC TATGTCATCA AAACAATATA          600

AAAACTAGAG CGATACCAAA GGAAATTTTA AATTCAAAAA CTAACTTGAA ATTAATATAT          660

TTAAAATTTC ATTTTTTTTT GTGTGGAGAA AACAAAGCAT AACACTTTGC TTTGTAACAC          720

TTTGCCTAGG TGAATGTCAG GGCTTATGCT CCACGATACT TATGCCCTGC CAGTACACCT          780

CGCAGTGGGA CTCGCTGAAA AAACGTCTTT GTTGTGAGAA ATTGCAATTT GAACCTCTA           840

CAATTTCGAC AAAACCTTGG TTCGTGAAAA CTGTTTGATT AACTTTTAGA CCATCCAGTC          900

AATTTAACTC TAAACTGACC TAAATAAATA CTACGTACAC TAGTCTTTAA GTTCATCAAA          960

GTGGACTCTG CATTAATAAT TGAAATTTAT GCCGCAACAA TGACATTAGG TTTTATAAAT         1020

AAAGTAATAG GAATTTGATA GTTCCAGGAA ACAACTCTAC AGTACTCCCT TATTTTGTGC         1080

CTTTTTAAAT AATATTATTC AGTTGACGAA ACAAATAAAT AAAATATTTG GAAACTGGA          1140

TCAATAGACC CCAGACGCCA ACAATGAATC AAAAGGCTGC TAGCTAGTGT AAAGTCTAGT         1200

AAGGCAACTG GGAAATTAAA TGATTAGGTG CTTTTGATCA ATTACATTAA CTAGTCTCTC         1260

ACCACTATAT ATACTTGTCC CTTCTCTTCC ATTTAAGTAG AGTTCCTTTC TTTCTTCCTT         1320

AAAACTTAAA AGAACAAGTA AAAATACACT CATCTTTAAT TAGCAATG                     1368

(2) INFORMATION FOR SEQ ID NO:6:

(i) SEQUENCE CHARACTERISTICS:
        (A) LENGTH: 9 base pairs
        (B) TYPE: nucleic acid
        (C) STRANDEDNESS: both
        (D) TOPOLOGY: linear (ii) MOLECULE TYPE: Genomic DNA (xi) SEQUENCE DESCRIPTION: SEQ ID NO:6:

CTACAGTAC                                                                       9

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: both
        (D) TOPOLOGY: linear (ii) MOLECULE TYPE: Genomic DNA (xi) SEQUENCE DESCRIPTION: SEQ ID NO:7:

GGGCTGCAGG CGTAAAGATA CATTATACC                                                 29

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: single
        (D) TOPOLOGY: both (ii) MOLECULE TYPE: Genomic DNA (xi) SEQUENCE DESCRIPTION: SEQ ID NO:8:

GGGCTGCAGG TGAATGTCAG GGCTTATGC                                                 29

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:9:

CTGGCAGGGC ATAAGTATCG                                                           20

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:10:

GGGCTGCAGT TCATCAAAGT GGACTCTGC                                                 29

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:11:

```
GGGCTGCAGA TTTGATAGTT CCAGGAAAC                                                 29

(2) INFORMATION FOR SEQ ID NO:12:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: Genomic DNA (xi) SEQUENCE DESCRIPTION: SEQ ID NO:12:

AGTACTGTAG ANTTGTTTCC                                                           20

(2) INFORMATION FOR SEQ ID NO:13:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: Genomic DNA (xi) SEQUENCE DESCRIPTION: SEQ ID NO:13:

GGNNNNNNGA TCAATAGACC                                                           20

(2) INFORMATION FOR SEQ ID NO:14:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: Genomic DNA (xi) SEQUENCE DESCRIPTION: SEQ ID NO:14:

GGGCTGCAGG GGTCTATTGA TCCAGTTTCC                                                30

(2) INFORMATION FOR SEQ ID NO:15:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: Genomic DNA (xi) SEQUENCE DESCRIPTION: SEQ ID NO:15:

GGGGATCCTG CTAATTAAAG ATGAGTG                                                   27

(2) INFORMATION FOR SEQ ID NO:16:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (ii) MOLECULE TYPE: Genomic DNA (xi) SEQUENCE DESCRIPTION: SEQ ID NO:16:

CAAAATAAGG GAGTACACTA GAGTTGTTTC C                                              31

(2) INFORMATION FOR SEQ ID NO:17:
```

```
        (i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:17:

AGCTACTCTA CAGTACTC                                                      18

(2) INFORMATION FOR SEQ ID NO:18:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:18:

AGCTGAGTAC TGTAGAGT                                                      18

(2) INFORMATION FOR SEQ ID NO:19:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:19:

CAACTCTACA GTACTCCC                                                      18

(2) INFORMATION FOR SEQ ID NO:20:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:20:

CAACTCTAGT GTACTCCC                                                      18
```

TRANSCRIPTIONAL SILENCING ELEMENTS AND THEIR BINDING FACTORS

CROSS REFERENCE TO RELATED APPLICATION

This application claims priority to provisional application 60/020,087, filed Jun. 13, 1996. +gi

STATEMENT AS TO FEDERALLY SPONSORED RESEARCH

This invention was made in part with Government funding, and the Government therefore has certain rights in the invention.

BACKGROUND OF THE INVENTION

This application relates to nucleotide regulatory sequences and their binding factors.

Plants have evolved a diverse array of mechanisms for protection against a variety of pathogenic organisms. Pathogen-derived signals such as elicitins, harpins, fungal cell wall fragments, avirulence (avr) gene products, and metabolites specified by avr gene products are recognized by receptors that trigger a conserved set of defense responses. Perception of these signals induces changes in protein phosphorylation that are thought to affect a variety of defense responses. Such defense responses include lignification of cell walls, induction of pathogenesis-related (PR) genes such as those encoding chitinases and glucanases, production of antimicrobial phytoalexins, induction of systemic acquired resistance, and generation of reactive oxygen species involved in crosslinking of cell wall proteins and induction of programmed cell death. These responses are instrumental in suppressing the growth and spread of a pathogen within the plant host.

Many of these defense responses are dependent on the transcriptional induction of specific genes in response to appropriate signals. For example, when solanaceous plants such as tobacco and potato are challenged by a pathogen or elicited by various pathogen factors, a major metabolic shift occurs where sterol production is suppressed and sesquiterpene phytoalexin synthesis is induced. The first step specific to sesquiterpene phytoalexin biosynthesis is a cyclization of the isoprenoid intermediate FPP by enzymes generically referred to as sesquiterpene cyclases. In tobacco, the sesquiterpene cyclase 5-epi-aristolochene synthase (EAS) produces 5-epi-aristolochene, followed by the addition of two hydroxyl groups to yield capsidiol. The sterol-specific branch of the isoprenoid biosynthetic pathway also extends from the intermediate FPP. Declines in sterol biosynthesis have been correlated with suppression of squalene synthase enzyme activity, and the induction of sesquiterpene biosynthesis with an induction of a sesquiterpene cyclase enzyme activity. Because these two enzymes are positioned at a putative branch point in the pathway, the induction of one enzyme and the suppression of the other were interpreted as an important mechanism controlling carbon flow and, hence, end product formation.

SUMMARY OF THE INVENTION

In general, the invention features an isolated nucleic acid sequence that includes an isoprenoid synthase gene silencing regulatory element. Preferably, such a isolated nucleic acid sequence includes the sequence 5' NTACNNTACN 3' (where N is A, T, G, or C) (SEQ ID NO: 1); for example, 5' CTACAGTACT 3' (SEQ ID NO: 2). In preferred embodiments, the nucleic acid of the invention includes the 5' TCTACAGTACT 3' (SEQ ID NO: 3) or 5' ACTCTACAGTACTC 3' (SEQ ID NO: 4) sequences. In yet other preferred embodiments, the isoprenoid synthase is a sesquiterpene synthase (e.g., epi-5-aristolochene synthase (EAS)).

In preferred embodiments, the nucleic acid sequence is from a dicot (e.g., a member of the Solanaceae such as Nicotiana). In other preferred embodiments, the nucleic acid sequence is from a monocot, a gymnosperm, or a conifer.

In related aspects, the invention features a vector or a transgenic plant (or a seed or plant cell thereof) that includes an isoprenoid synthase gene silencing regulatory element. In general, the vector containing the silencing element of the invention reduces or eliminates the expression of an operably linked nucleotide sequence in a vector-containing cell (e.g., a transgenic plant cell).

In another aspect, the invention features a method for decreasing the transcription of a DNA sequence in a transgenic plant. This method involves the steps of: (a) providing a transgenic plant cell which includes the nucleic acid of an isoprenoid synthase gene silencing regulatory element positioned for decreasing transcription of a DNA sequence and integrated into the genome of said transgenic plant cell; and (b) growing said transgenic plant from said transgenic plant cell.

In another aspect, the invention features factors, e.g., a polypeptide, that bind to an isoprenoid synthase gene silencing regulatory element.

By "gene silencing regulatory element" is meant a nucleic acid sequence capable of negatively regulating the expression of a gene product. Such silencing elements function to reduce or eliminate the expression of a gene. Repression of a gene silencing regulatory element results in the activation of gene expression, e.g., transcription of the EAS4 gene promoter described herein. In general, gene silencing regulatory elements are located in the 5' region of a gene, e.g., in the promoter region. Multiple copies of such gene silencing elements may also be used to reduce or eliminate gene expression.

By "positioned for decreasing transcription of a DNA sequence" is meant that a silencing regulatory element is positioned to decrease or eliminate expression of a gene that is under the control of such a regulatory element. Such silencing elements, in general, are sufficient to render promoter-dependent gene expression controllable for cell- or tissue-specific gene expression, or gene expression that is inducible by external signals or agents; such elements may be positioned in the 5' or 3' regions of a gene. In addition, the position of a silencing element for decreasing or inhibiting transcription is independent of both its orientation and distance from a transcription start site. In general, silencing elements of the invention reduce transcription of gene expression by at least 10%. Preferably, the reduction of transcription is at least 20%, more preferably at least 40%, and most preferably 90% relative to a transcriptional regulatory region that does not contain a silencing element.

By "obtained from a gene" is meant that the nucleotide sequence of a regulatory element is based on sequence information included in a naturally-occurring plant gene (e.g., the EAS4 promoter region of Nicotiana). Once identified, the silencing regulatory element according to the invention is obtained from a natural source or can be prepared according to any standard method (e.g., by recombinant methods or chemical synthesis).

By "isoprenoid synthase gene" is meant a gene that encodes a polypeptide which is capable of catalyzing a reaction involving the intramolecular carbon-carbon bond formation of an allylic diphosphate substrate (for example, a $C_{10}$, $C_{15}$, or $C_{20}$ allylic diphosphate substrate) to an isoprenoid product (for example, a monoterpene, diterpene, sesquiterpene, or sterol product). Examples of such isoprenoid synthase genes include, without limitation, monoterpene synthases (for example, limonene synthase), diterpene synthases (for example, casbene synthase), and sesquiterpene synthases (for example, 5-epi-aristolochene synthase, vetispiradiene synthase, and cadinene synthase) that are responsible for cyclization of geranyl diphosphate (GPP), geranylgeranyl diphosphate (GGPP), famesyl diphosphate (FPP), respectively.

By "epi-5-aristocholene synthase" or "EAS" is meant an enzyme capable of catalyzing the cyclization of trans, trans-farnesyl diphosphate to the bicyclic intermediate epi-5-aristocholene.

By "operably linked" is meant that an isoprenoid synthase gene silencing regulatory element and a plant transcriptional regulatory region are connected in such a way as to reduce or eliminate gene expression when the appropriate molecules (e.g., transcriptional proteins) are bound to the silencing regulatory sequence(s).

By "polypeptide" is meant any chain of amino acids, regardless of length or post-translational modification (e.g., glycosylation or phosphorylation).

By "transformed plant cell" is meant a cell into which (or into an ancestor of which) a recombinant nucleotide sequence (e.g., the EAS4 promoter) has been introduced by means of recombinant DNA techniques (e.g., those techniques described herein).

By "plant cell" is meant any self-propagating cell bounded by a semi-permeable membrane and containing a plastid. Such a cell also requires a cell wall if further propagation is desired. Plant cell, as used herein includes, without limitation, algae, cyanobacteria, seeds, suspension cultures, embryos, meristematic regions, callus tissue, leaves, roots, shoots, gametophytes, sporophytes, pollen, and microspores.

By "transgenic" is meant any cell which includes a DNA sequence which is inserted by artifice into a cell and becomes part of the genome of the organism which develops from that cell. As used herein, the transgenic organisms are generally transgenic plants, and the DNA is inserted by artifice into the genome of the organism.

By "isolated DNA" is meant DNA that is free of the sequences which, in the naturally-occurring genome of the organism from which the DNA of the invention is derived, flank it. The term therefore includes, for example, a recombinant DNA silencing regulatory element which is incorporated into a vector; into an autonomously replicating plasmid or virus; or into the genomic DNA of a prokaryote or eukaryote; or which exists as a separate molecule (e.g., within a promoter region) independent of other sequences. It also includes a recombinant DNA regulatory element which is part of a hybrid gene that encodes a polypeptide sequence.

Other features and advantages of the invention will be apparent from the following description of the preferred embodiments thereof, and from the claims.

BRIEF DESCRIPTION OF THE DRAWINGS

FIG. 1A is a schematic illustration showing the map of the EAS4 promoter region. The location of polymerase chain reaction (PCR) primers used for cloning and producing various probes and competitors are shown as small arrows and fragments having letter designations A–E. The large arrow at the right of the map represents the EAS4 open reading frame. The bent arrow with the +1 designation indicates the EAS4 transcription start site (position 1299 (5' GTA $^{+1}$G 3') as depicted in SEQ ID NO: 5); and the position of the TAC-box is designated by a solid vertical rectangle enclosed within Fragment C.

FIG. 2B is an illustration showing the nucleotide sequences of the WT-TAC-Box and the M2-TAC-Box. The underlined sequences in WT-TAC-Box show the reiterated TAC-box, and stars indicate the positions where methylation of guanine interferes with protein binding. The boxed nucleotides in M2-TAC-Box represent nucleotides mutated using site-directed mutagenesis.

DETAILED DESCRIPTION OF THE INVENTION

There now follows a description of an analysis of DNA-binding activities that recognize specific sequences on the promoter region of the 5-epi-aristolochene synthase gene designated EAS4. The binding site of one activity was identified by footprinting methods, and then mutated to determine the effect on protein binding and promoter activity. The DNA binding activity was characterized biochemically, and the protein responsible for this activity was purified. In addition, functional identification of this cis-element in the EAS4 promoter was verified by transforming into tobacco a series of promoter constructs containing the silencing element fused to the GUS reporter gene.

Figure 1B:
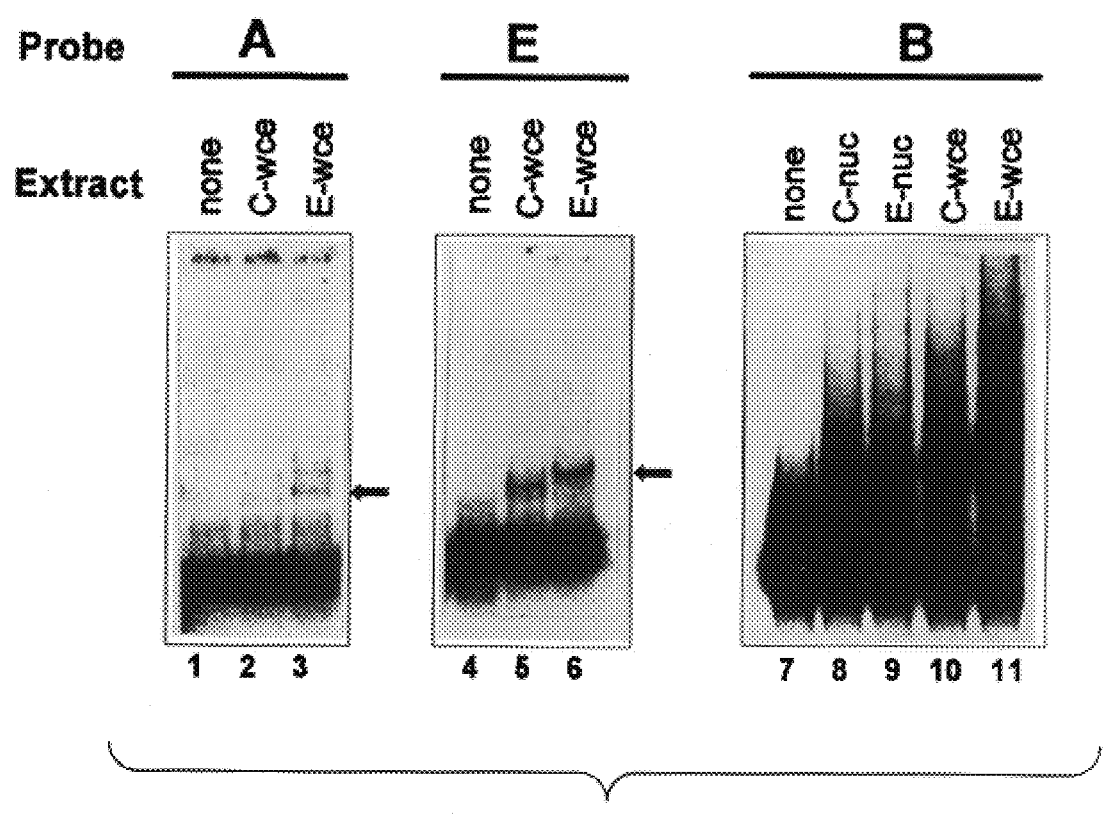
FIG. 1B is a panel of photographs showing the results of electrophoretic mobility shift assays (EMSA) using Fragments A, E, and B in the presence of nuclear and whole cell extracts that were prepared from control and elicitor-treated cells. Binding assays contained one microgram dI-dC, one nanogram radiolabelled DNA probe, and two nanograms of protein extract. Nuclear (designated nuc) and whole cell extracts (designated wce) were prepared from control cells (designated C) or cells that were elicited with cellulase (designated E) for three hours.

These examples are provided for the purpose of illustrating the invention, and should not be construed as limiting.
Identification of EAS Promoter Region Binding Activity To understand the mechanism by which the EAS4 gene is regulated, the EAS promoter region (SEQ ID NO: 5) was divided into five overlapping nucleotide fragments, designated Fragments A–E (FIG. 1A), and each fragment was examined for its ability to bind proteins that were prepared from nuclear or whole cell extracts of tobacco cell suspension cultures. These experiments showed that no specific DNA-binding activities to Fragments A or E were detected in nuclear extracts when examined using electrophoretic mobility shift assays (EMSA) (data not shown). Because proteins can be lost while preparing isolated nuclei, whole cell extracts were also examined for their ability to bind Fragments A–E.

Figure 1C:
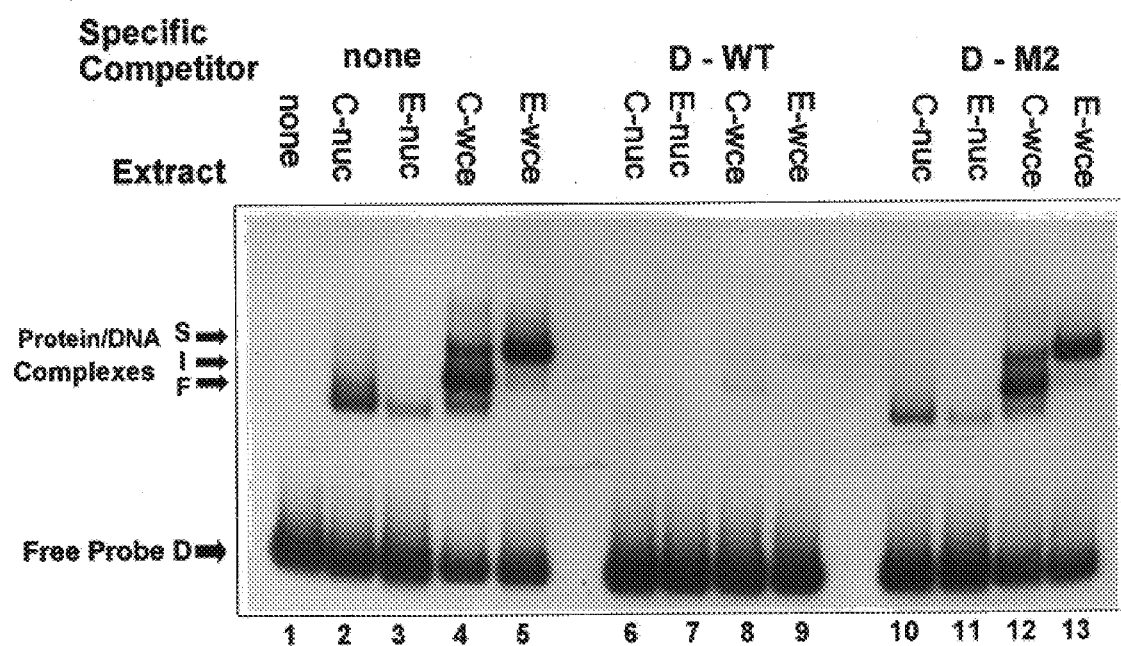
FIG. 1C is a photograph showing the results of electrophoretic mobility shift assays using Fragment D that were incubated in the presence of nuclear (designated nuc) and whole cell (designated wce) extracts prepared from control or elicitor-treated cells. Assays were performed as in FIG. 1B, except that a 50-fold molar excess of wild-type Fragment D or Fragment D containing mutation M2 (as illustrated in FIG. 2B) was included as specific competitors in these assays.

The results of these experiments indicated that several weak binding activities to Fragments A–E were present in whole cell extracts (FIG. 1B, lanes 1–6), and a major DNA-binding activity was observed in nuclear and whole cell extracts was observed that bound Fragments B (FIG. 1B, lanes 7–11) and D (FIG. 1C, lanes 1–5). Restriction enzyme analysis indicated that the major DNA-binding activity recognized a sequence in a region where these two fragments overlapped (data not shown). As shown in FIG. 1C, three migrating complexes (designated F, I, and S referring to fast, intermediate, and slow-migrating complexes, respectively) were observed in binding reactions prepared using Fragment D and different extracts. Nuclear extracts from both control (C-nuc) and elicitor-treated (E-nuc) cells formed the fast migrating complex, and this DNA-binding activity was less abundant in nuclear extracts that were prepared from elicitor-treated cells.

Control whole cell extract formed all three complexes, with complex I (intermediate) being the most abundant. Whole cell extracts prepared after elicitor-treatment for three hours predominantly formed complex S (slow). The addition of a fifty-fold excess of unlabelled Fragment D (FIG. 1C, lanes 6–9) reduced the amount of labelled Fragment D that was bound, thereby demonstrating sequence specificity.

Identification of a Protein Binding Site

Figure 2A:
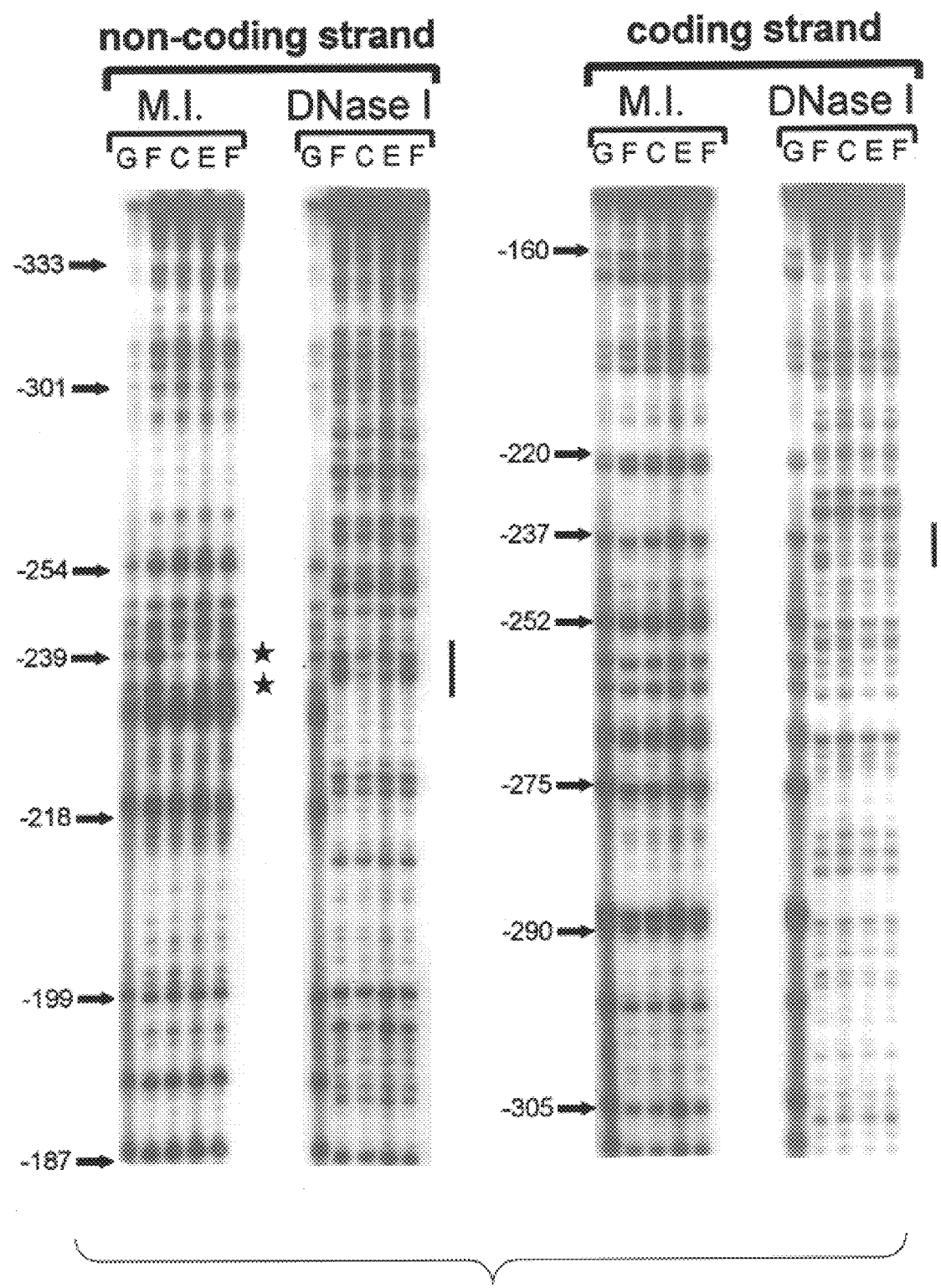
FIG. 2A is a panel of photographs illustrating the identification of the major protein binding site in the EAS4 promoter. Methylation interference (M.I.) and DNaseI (DNase) footprinting analyses were performed using Fragment C labeled at the 5' end of the coding or non-coding strand. Stars indicate the positions where methylation of guanine bases interferes with protein extract binding. Solid lines define regions that were partially protected from DNaseI cleavage. Lane marker designations are as follows: G refers to guanine-specific cleavage reaction; F refers to free (unbound) DNA after electrophoretic mobility shift assay (EMSA); C refers to DNA bound by control nuclear extract; and E refers to DNA bound by protein in nuclear extract from elicitor-treated cells.

To identify the specific nucleotide bases comprising the binding site for the activity identified above, methylation interference (M.I.) and DNase I footprinting experiments were performed (FIG. 2A). Fragment C of the EAS promoter region was partially methylated on guanines, mixed with nuclear protein from control or elicitor-treated cells, and analyzed using EMSA to separate the bound from unbound DNA. After gel purification, the DNA was cleaved at the methylated sites and the resulting fragments were resolved on a denaturing 6% polyacrylamide sequencing gel (FIG. 2A). DNA fragments methylated on the non-coding strand guanines at positions −239 and −234 (FIG. 2A—designated by stars) were underrepresented in the bound DNA fractions (FIG. 2A, lanes C and E), indicating that methylation at these positions interfered with protein binding. Methylation of the guanine at position −237 of the coding strand had no effect on DNA binding.

DNase I footprinting analysis also implicated this same region within Fragment C as the protein binding site. In the presence of nuclear extract prepared from either control or elicitor-treated cells, the region from −237 to −242 of the coding strand and from −236 to −242 on the non-coding strand was partially protected from DNaseI digestion (FIG. 2A, solid lines). These observations provided additional evidence that the DNA-protein complexes that formed in the presence of Fragments B and D were due to binding where these two fragments overlapped (i.e., within Fragment C). Together the results from methylation interference and DNaseI footprinting indicated that this nucleotide sequence was indeed recognized by the DNA-binding activity found in nuclear extract prepared from control and elicitor-treated cells. This sequence, 5' CTACAGTAC 3' (SEQ ID NO: 6) as been designated the TAC-box, due to the presence of reiterated "TAC" motifs.

To confirm that the TAC-box was responsible for the binding activities observed by EMSA, two nucleotides within the TAC-box were altered via oligonucleotide mediated site-directed mutagenesis (FIG. 2B, M2-TAC-Box). A DNA fragment containing the mutated TAC-box was minimally bound by nuclear and whole cell extracts from control and elicitor-treated cells (data not shown) and did not compete the binding of wild type Fragment D probe (FIG. 1C, lanes 10–13). This result provided further evidence indicating that the TAC-box element is required for protein binding.

Characterization of TAC-Box Binding Activity

Figure 3A:
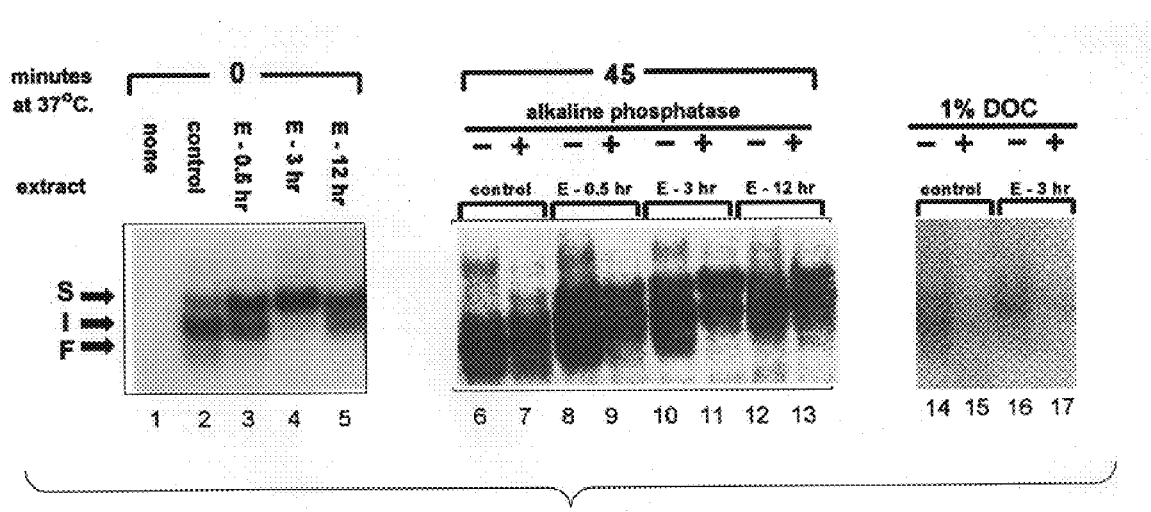
FIG. 3A is a photograph of an EMSA that was performed using extracts prepared from control cells (lanes 2, 6, and 7) or cells treated with elicitor for one-half hour (lanes 3, 8, and 9), three hours (lanes 4, 10, and 11), or twelve hours (lanes 5, 12, and 13). Proteins were diluted to one microgram per microliter with alkaline phosphatase assay buffer and then immediately added to binding reaction mixtures (lanes 2–6); or were added after forty-five minutes of incubation at 37° C. without (lanes 6, 8, 10, and 12) or with (lanes 7, 9, 11, and 13) alkaline phosphatase. Binding reactions for EMSA contained 0.5 pmole TAC-box double stranded oligonucleotide probe, two picograms of poly dI-dC, and two micrograms protein extract in a total volume of ten microliters. Only the portion of the gels containing the protein-DNA complexes are shown in FIGS. 3A–3C.

The differences in the migration of TAC-box-protein complexes between whole cell extracts from control and elicitor-treated cells suggested that the TAC-box binding factor might undergo modification during the course of the cellular response resulting from elicitor treatment. To examine this possibility, whole cell extracts were prepared from cells treated with elicitor for varying amounts of time (FIG. 3A, lanes 1–5). Previous studies indicated that EAS mRNA accumulation is most rapid from two to six hours following elicitor-treatment. After this time mRNA levels began to decrease and returned to control levels by twenty-four hours. While whole cell extracts prepared from control cells generated predominantly complex I; whole cell extracts prepared from cells treated with elicitor for thirty minutes generated the formation of complex S, although complex I was also identified in whole cell extracts prepared from cells at the peak of EAS transcription (i.e., three hours after elicitor treatment) formed complex S; and whole cell extracts prepared from cells twelve hours after elicitor treatment formed complex I. These results indicated that alterations in the TAC-box-protein complex are correlated with the induction pattern of EAS gene transcription.

To examine the nature of the differences in complex migration, the effect of dephosphorylation on binding activity (FIG. 3A, lanes 6–13) was examined. Whole cell extracts were diluted approximately ten-fold in alkaline phosphatase buffer (20 mM Tris-HCl, pH 8.5), and the extracts were incubated at 37° C. for forty-five minutes prior to EMSA analysis. Surprisingly, the protein-DNA complexes were found to shift from slower to faster migrating forms when the extracts were incubated at 37° C. in the absence of alkaline phosphatase (compare lanes 2 and 6; 3 and 8; 4 and 10; and 5 and 12 of FIG. 3A). Incubation with alkaline phosphatase therefore decreased the total amount of binding activity, and also partially inhibited the shift in complex migration. In separate experiments, a thirty minute incubation at 37° C. with or without alkaline phosphatase had no effect on the binding activity of the nuclear extracts (data not shown).

Figure 3B:
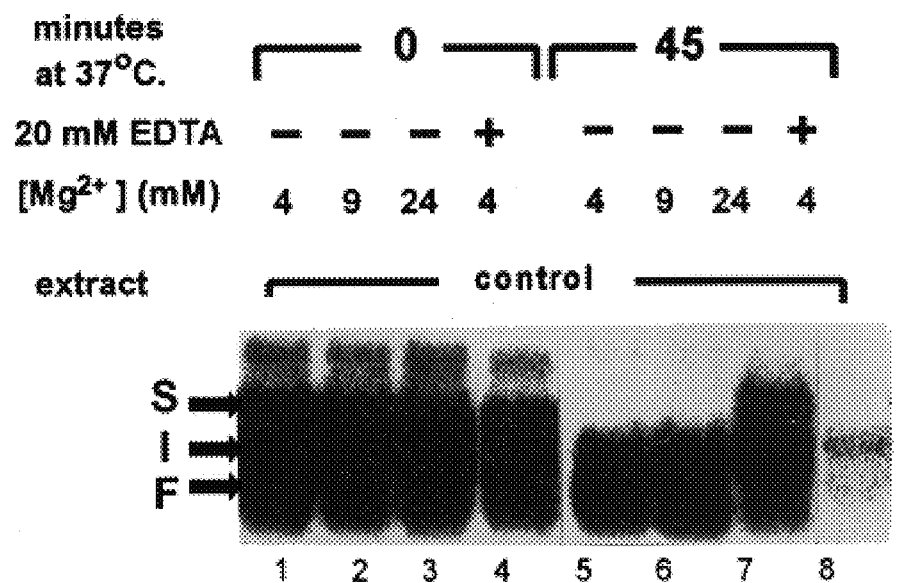
FIG. 3B is a panel of photographs showing an EMSA using protein extracts prepared from control whole cell extracts that were diluted to one microgram per microliter in binding buffer that was supplemented with $MgCl_2$ or EDTA and was added to binding assays immediately (lanes 1–4); or was added to the binding assays after incubation at 37° C. for forty-five minutes (lanes 5–8).

To determine the lack of shift in complex migration under these conditions, whole cell extracts prepared from control cells were diluted and supplemented with $MgCl_2$ or EDTA, and this mixture was then immediately added to binding assays or, alternatively, incubated for forty-five minutes at 37° C. prior to addition of $MgCl_2$±EDTA (FIG. 3B). EMSA revealed that the presence of $MgCl_2$ or EDTA did not affect the migration of the TAC-box-protein complexes (FIG. 3B, lanes 1–4). After forty-five minutes the sample containing only 4 mM $Mg^{2+}$ produced mostly complex F; incubation with 9 mM $Mg^{2+}$ produced complexes F and I in equal abundance; and 24 mM $Mg^{2+}$ had no effect on complex mobility. In addition, EMSA of samples incubated with EDTA (FIG. 3B, lane 8) indicated that binding activity was inhibited, indicating that divalent cations are required for TAC-box protein binding. Our results also indicated that cell extracts prepared with buffers lacking $Mg^{2+}$ contained no TAC-box binding activity (data not shown).

Figure 3C:
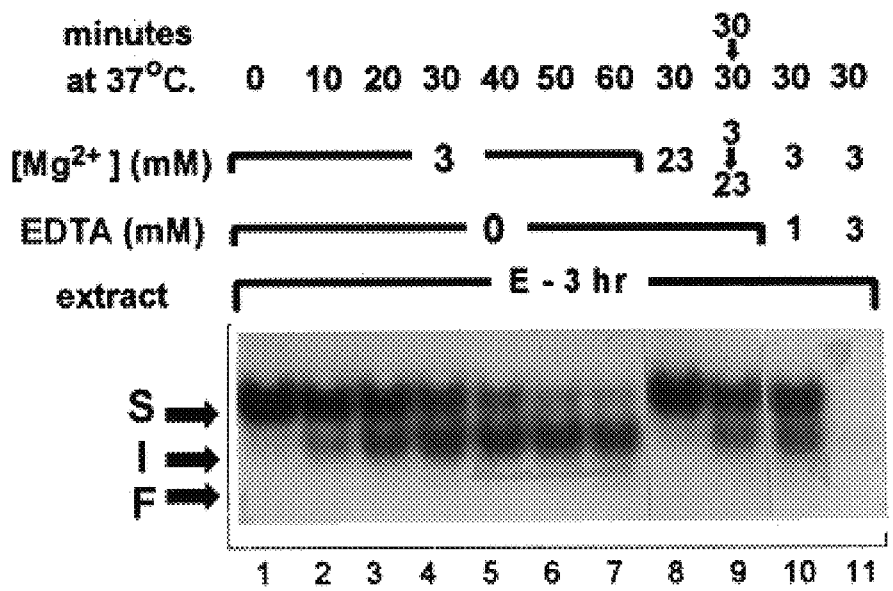
FIG. 3C is a photograph showing an EMSA using whole cell extracts prepared from three hour elicitor-treated cells with (lane 8) or without added $MgCl_2$ (lanes 1–7, 9–11) or EDTA (lanes 10, 11) and incubated at 37° C. for varying durations prior to addition to binding reactions. The extract used for lane 9 was first incubated for thirty minutes without $MgCl_2$.

The shifts in complex mobility after incubation of whole cell extracts prepared from elicitor-treated cells at 37° C. in the presence of low $Mg^{2+}$ concentrations were also monitored during a sixty minute incubation (FIG. 3C, lanes 1–7). During this period, a decrease in complex S was observed to coincide with an increase in complex I. In addition, a decrease in the total amount of TAC-box binding activity was observed. No changes in complex migration were observed when this extract was incubated with high $Mg^{2+}$ concentrations. Addition of $Mg^{2+}$ after thirty minutes of a total sixty minutes incubation period prevented alteration of the binding activity beyond that which occurred during the first thirty minutes. Again, incubation under these conditions in the presence of EDTA was found to inhibit TAC-box binding activity.

Purification of TAC-box Binding Factor

Figure 4A:
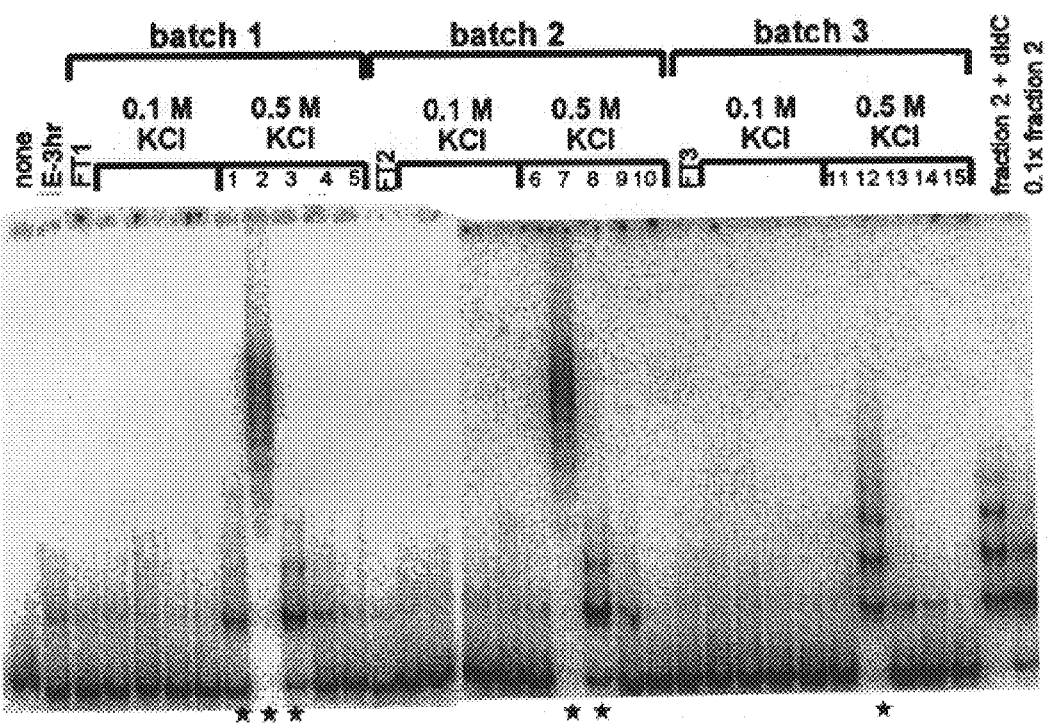
FIG. 4A is a photograph illustrating the EMSA of various fractions obtained from DNA affinity chromatography fractions. Ten microliters of binding assays containing one nanogram of Fragment C probe (FIG. 1A) and two micrograms of protein sample were loaded in each lane. The lane designated "E-3 hr" refers to the protein sample prepared from cells treated with elicitor for three hours that was loaded onto the column; batch 1 and batch 2 refer to two identical samples processed sequentially; and batch 3 refers to the combination of flow through (FT1 and FT2) and low salt (0.1 M KCl) washes that were combined and passed over the column a second time to extract additional binding activity. In the final three lanes, protein samples were diluted 10-fold (0.1X) or had 0.5 micrograms dI-dC added to the binding assay. Stars indicate fractions pooled and dialyzed to yield the preparation designated E-DAC, that was then ultrafiltered to yield the preparation designated E-DAC-UF.
Figure 5:
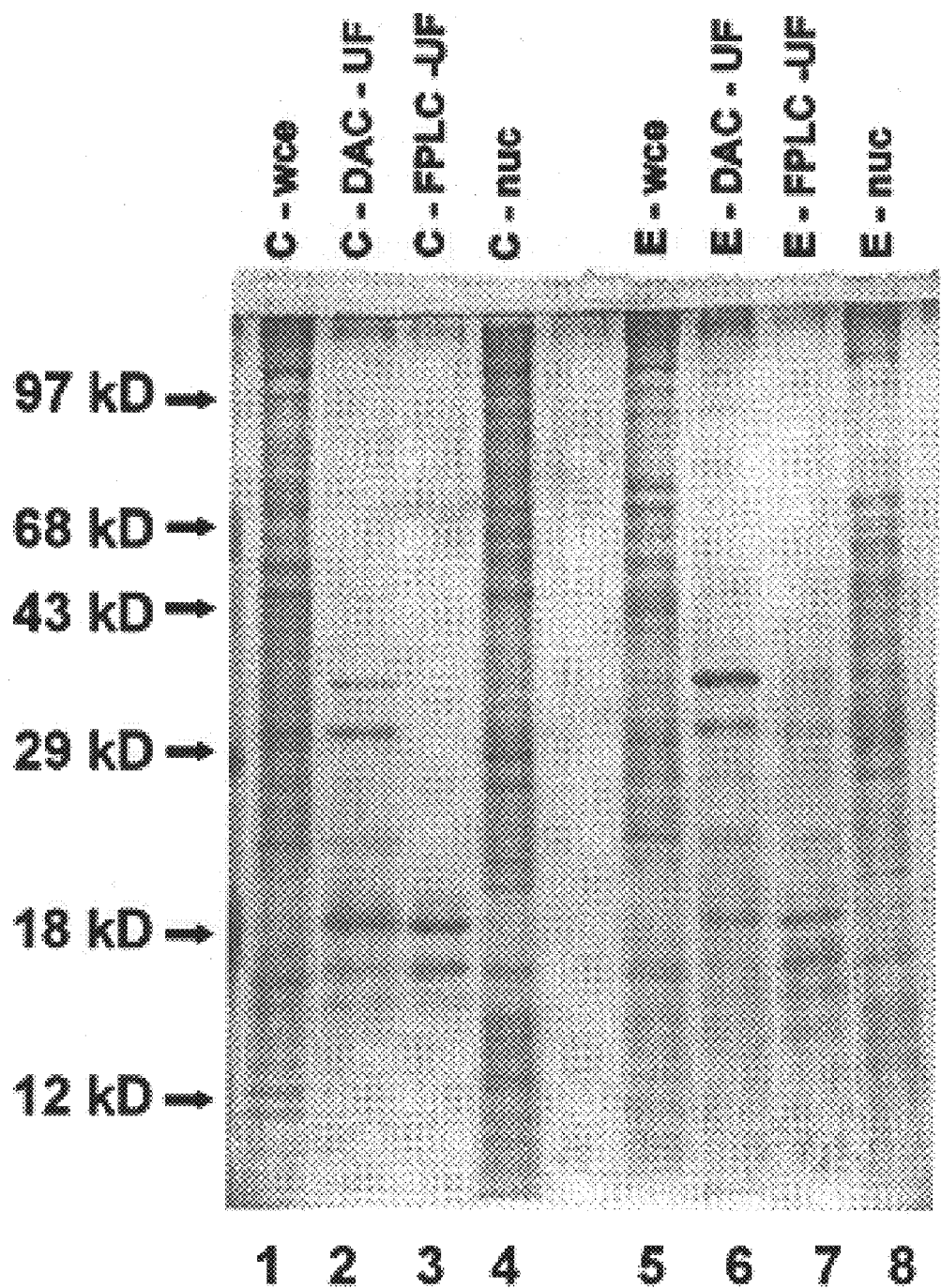
FIG. 5 is a photograph of an SDS-PAGE analysis of various TBBF preparations. Lane 1, control-whole cell extract; lane 2, C-DAC-UF; lane 3, C-FPLC-UF; lane 4, C-nuclease; lane 5, E-whole cell extract; lane 6, E-DAC-US; lane 7, E-FPLC-UF; and lane 8, E-nuc.

Several attempts to identify the TAC-box binding factor (TBBF) by southwestern blot as described by Miskimins et al. (*Proc. Natl. Acad. Sci.* 82:6741–6744, 1985) with crude protein extracts were unsuccessful. To further characterize this binding activity, we purified TBBF using DNA-affinity chromatography. Crude whole cell extract prepared from three hour elicitor-treated cells was mixed with fish sperm DNA in ZNG buffer to bind non-specific DNA-binding proteins. This mixture was divided into two batches and passed separately over a 5 mL bed volume TAC-box sepharose column. The column was then washed with ZNG buffer containing 0.1 M KCl to elute weakly bound proteins, and with ZNG buffer containing 0.5 M KCl to elute TBBF from the immobilized DNA affinity column. The first two flow through (referred to as FT1 and FT2) and low salt washes were combined and passed over the column a second time to extract the remaining binding activity (FIG. 4A). EMSA using (FT 1) exhibited less TAC-box binding activity than the crude sample that was applied to the column (E-3 hours), indicating that a large percentage of the DNA binding activity was retained on the column. Minimal TBBF eluted from the column during low salt washes; however, protein binding activity was eluted in the presence of 0.5 M KCl (FIG. 5, fractions 1–3, 7–8, 12). Note that these binding assays did not contain non-specific DNA, except that which was added to the extract before chromatography. Thus, fish sperm DNA was present in the original sample, the flow through eluants (FT1 and FT2), and the low salt washes, but not in the high salt fractions.

Preliminary experiments indicated that the affinity-purified TBBF was capable of binding DNA non-specifically, even after the high affinity binding sites had been occupied. Therefore, when TBBF was present in excess over the amount of probe, multiple proteins were observed to bind to a single DNA fragment. This resulted in the formation of a ladder, with each rung containing one more protein bound than the lower rung. In addition, this effect was visualized by comparing different amounts of a high-activity protein fraction or by adding non-specific DNA. Thus, the presence of a 500-fold excess of non-specific DNA (fraction 2+dI-dC) was found to decrease the number of higher-order complexes such that the majority of the probe was bound by only one or two TAC-box binding factors. Decreasing the amount of TBBF added to the binding assays by 90% (0.1×fraction 2) had the same effect as adding non-specific DNA. Finally, when a double-stranded oligonucleotide was used as the probe, one complex was found to form, even when the amount of binding activity was present in excess (data not shown).

High salt fractions containing the binding activity (~30 mL) were combined and dialyzed against ZNG buffer lacking KCl, and ultrafiltered to approximately 5 mL. Analysis of these processed DNA-affinity chromatography fractions and a similar preparation from control cells by SDS-PAGE and silver staining revealed five to seven major polypeptide bands (FIG. 5, lanes 2 and 6). Since southwestern blot analysis again failed to identify a specific band as the TAC-box binding protein, the partially purified protein preparation was further fractionated by fast-protein liquid chromatography (FPLC).

To determine the appropriate ion exchange column for this purification step, aliquots of the partially purified TBBF were mixed with the anion exchange resin Q-sepharose or the cation exchange resin S-sepharose. After centrifugation and removal of the supernatant containing unbound protein, the sepharose was washed consecutively with ZNG buffer and with ZNG buffer containing 1.0 M KCl. Analysis of the binding activity in each fraction by EMSA revealed that TBBF bound S-sepharose but not Q-sepharose (data not shown).

Figure 4B:
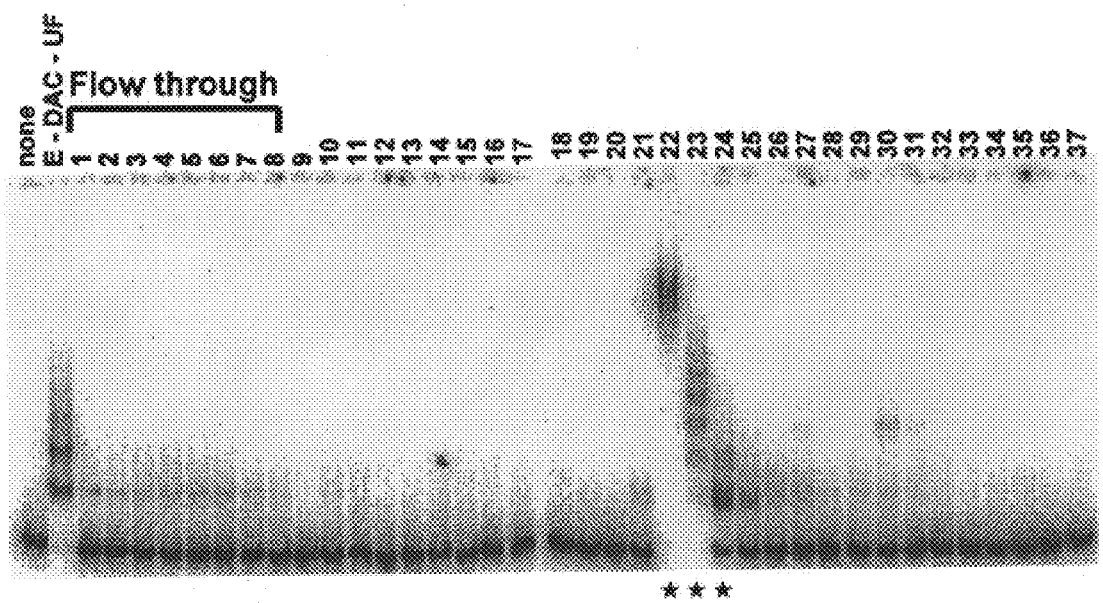
FIG. 4B is a photograph illustrating EMSA analysis of various fractions obtained during Mono-S fast protein liquid chromatography (FPLC). Binding assays were performed as above, except that two microliters of a 10-fold dilution of each fraction was used. E-DAC-UF refers to the sample loaded onto the gel, and numbers correspond to specific one milliliter fractions obtained from the column. Stars indicate fractions pooled and dialyzed to yield the preparation designated E-FPLC, which was then ultrafiltered to yield the preparation E-FPLC-UF.

The DNA-affinity chromatography purified TBBF preparations were then loaded onto a Mono-S column, and the bound proteins were eluted using a linear gradient of KCl in Z buffer. As shown in FIG. 4B, fractions one through eight which corresponded to the initial flow through of the column, contained only a small amount of TAC-box binding activity as compared to the (E-DAC-UF) sample that was loaded onto the column. Although little binding activity was eluted in the presence of low KCl concentrations, protein binding activity was eluted rapidly when the level of KCl reached approximately 150 mM (FIG. 4B, fractions 22 through 24). These fractions were pooled, desalted, and concentrated by ultrafiltration. The fractions were then stabilized with glycerol and stored at −80° C.

Purification of TBBF was qualitatively assessed using SDS-PAGE, and the separated proteins were then visualized using silver-staining (FIG. 5A). The FPLC-purified sample from control cells showed two major bands at 17 and 19 kD in approximately equal abundance. Minor polypeptide bands were detected at 16 and 20 kD (FIG. 5A, lane 3). A similar preparation from elicitor-treated cells contained contaminating protein but the 17 and 19 kD polypeptides were visible, indicating that these polypeptides were the principal components of TBBF. Polypeptides of 23, 31, and 37 kD were found to co-purify with TBBF during DNA-affinity chromatography using extracts that were prepared from both the control and elicitor-treated cells (FIG. 5, compare lanes 2 and 6). The decreased abundance of the 37 kD band in the preparation from control cells relative to that from elicitor-treated cells was not likely to be significant since a different preparation from control cells showed the presence of this band in higher amounts. Nuclear extracts from control and elicitor-treated cells also contained a strong band that comigrated with the 17 kD band of purified TBBF, whereas the nuclear extract band that co-migrated with the 19 kD polypeptide was relatively weak.

To quantify the amount of DNA binding activity recovered after each purification step, EMSA was performed in the presence of an excess concentration of double-stranded oligonucleotide containing the TAC-box DNA element. While the larger Fragment C probe that was used to monitor binding activity during purification was valuable for the visual identification of fractions with high levels of binding activity, utilization of a probe that bound one factor was required for quantitation. Non-specific competitor DNA was not present in these quantitative assays. As a result, non-specific DNA-binding proteins that formed similarly-migrating complexes likely caused a slight overestimate in the activity measurement with crude extracts, but not with the purified preparations. With this in mind, TBBF was purified at least 750-fold and 461-fold from control and three hour elicitor-treated cells, respectively (Table I).

TABLE I

Purification of TBBF from control and elicitor-treated cell cultures.

| Sample | volume (mL) | protein ($\mu$g) | activity (units$^a$ × $10^{-3}$) | recovery (%) | sp.activity (units/$\mu$g) | fold purif. |
|---|---|---|---|---|---|---|
| C-WCE | 11 | 180,000 | 3487 | 100 | 19.4 | — |
| C-DAC | 70 | 280 | 990 | 28.4 | 3536 | 182 |
| C-DAC-UF | 8 | 256 | 1043 | 29.9 | 4073 | 210 |
| C-FPLC | 4 | 25 | 237 | 6.8 | 9487 | 489 |
| C-FPLC-UF | 0.5 | 17.9 | 260 | 7.5 | 14551 | 750 |
| E-WCE | 3 | 50,000 | 811 | 100 | 16.2 | — |
| E-DAC | 27 | 216 | 284 | 35.1 | 1316 | 81 |
| E-DAC-UF | 5 | 185 | 267 | 33 | 1444 | 89 |
| E-FPLC | 3 | 30 | 175 | 21.5 | 5817 | 359 |
| E-FPLC-UF | 0.275 | 11 | 82 | 10.1 | 7469 | 461 |

$^a$One unit of binding activity is defined as the amount of activity necessary to bind 1 fmole of double stranded TAC-box oligonucleotide probe.

Characterization of the Purified Protein

The FPLC-purified TBBF preparation from three hour elicitor-treated cells was also used in a quantitative footprint analysis to examine the relative specificity of the binding activity, or preference for the TAC-box over non-specific DNA. In each experiment, Fragment C (8.8 fmole) was labelled on the coding strand and the labelled fragment was incubated with increasing amounts of TBBF, while the amount of poly dI-dC or fish sperm DNA was varied between experiments. After DNaseI treatment and precipitation, the DNA was separated on a sequencing gel and analyzed.

Figure 6A:
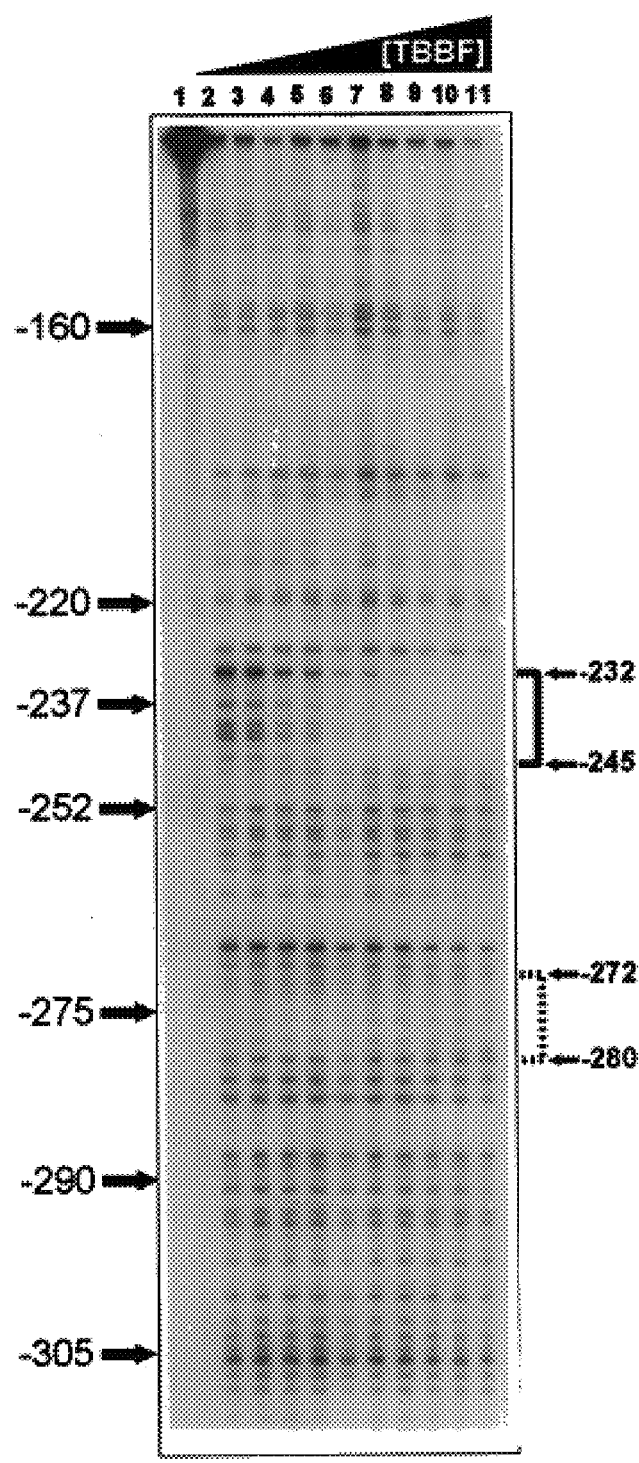
FIG. 6A is a photograph of a DNase I footprinting analysis using purified TBBF preparations.

A representative series of experiments with increasing amounts of TBBF is shown in FIG. 6A, with the primary footprint indicated by the solid bracket. We observed that the footprint with the protein purified from whole cell extracts was larger than the footprint with the crude nuclear extract (FIG. 2A). This footprint clearly extended from the strong band at −232 down to the band corresponding to −245, neither of which was protected by the crude nuclear extracts. This extended footprint included the two ACTC motifs spaced exactly 10 bp apart, and therefore on the same face of the helix. We also observed that there was a slight change in the DNase I sensitivity pattern at approximately −275 in the presence of very large amounts of TBBF (dashed bracket). This area has the nucleotide sequence TAaAG-TAaT (lower case letters refer to non-matching nucleotides), which matches the core TAC-box sequence at seven of nine positions.

Figure 6B:
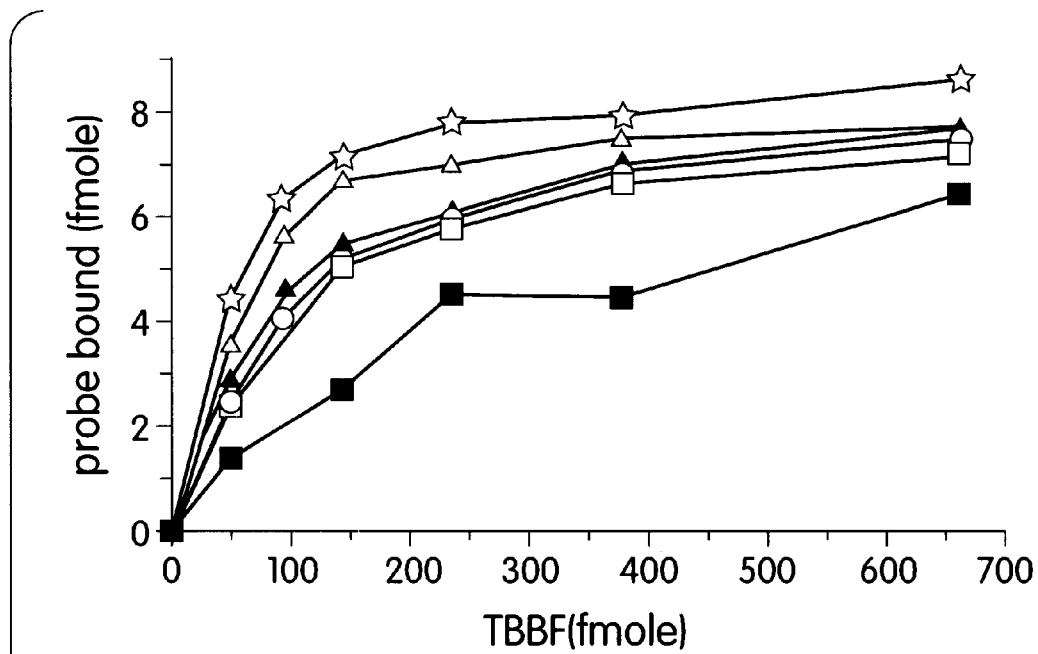
FIG. 6B is a graph showing the amount of TBBF bound to TAC-box probe in the presence of various non-specific DNAs.

Quantitative analysis revealed that, as the protein concentration increased, the percentage of bound probe increased to 100% (FIG. 6B). Fish sperm DNA (fs DNA) inhibited binding of the probe and was found to increase the dissociation constant ($K_d$) to a greater extent than dI-dC, presumably due to the random occurrence of the TAC-box ing strand (c) or noncoding strand (n) within the EAS4 promoter (see below and FIG. 1A). Bases shown in lower case correspond to nonhomologous bases added to incorporate a restriction site or mutation (n is A, T, G, or C).

```
-740c      gggctgcAGGCGTAAAGATACATTATACC      (SEQ ID NO: 7)
-571c      gggctgcAGGTGAATGTCAGGGCTTATGC      (SEQ ID NO: 8)
-526n      CTGGCAGGGCATAAGTATCG               (SEQ ID NO: 9)
-349c      GggcTgcAGTTCATCAAAGTGGACTCTGC      (SEQ ID NO: 10)
-266c      GggcTgcagATTTGATAGTTCCAGGAAAC      (SEQ ID NO: 11)
-233n      AGTACTGTAGAnTTGTTTCC               (SEQ ID NO: 12)
-160c      GgnnnnnnGATCAATAGACC               (SEQ ID NO: 13)
-147n      gGGCtgCaGGGGTCTATTGATCCAGTTTCC     (SEQ ID NO: 14)
+76n       GgGGatccTGCTAATTAAAGATGAGTG        (SEQ ID NO: 15)
TAC-M2n    CAAAATAAGGGAGTACAcTAGAGTTGTTTCC    (SEQ ID NO: 16)
dsTACc     agctACTCTACAGTACTC                 (SEQ ID NO: 17)
dsTACn     agctGAGTACTGTAGAGT                 (SEQ ID NO: 18)
``` element in fish sperm DNA. Under all conditions examined, the Kd ranged from $1.5 \times 10^{-10}$M to $1.5 \times 10^{-9}$M.

TAC-Box Element Functions as a Silencer

Figure 7A:
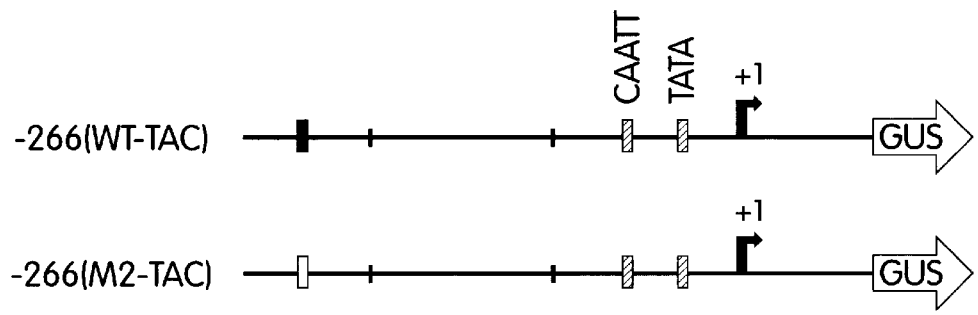
FIG. 7A is a schematic illustration showing the location of the wild-type TAC-box element (WT-TAC-Box) and the mutated TAC-box element (M2-TAC-Box) in the EAS4 promoter:GUS gene fusions.

Transgenic tobacco plants containing promoter fusions to the β-glucuronidase (GUS) coding region were constructed to assess the function of the TAC box (FIG. 7A). The chimeric gene fusions consisted of the EAS4 5'-untranslated region and 266 nucleotides upstream of the EAS transcription start site and included either the wild type or mutated TAC box. F1 plants were grown to the ten to twelve leaf stage and two young, fully expanded leaves were infiltrated on opposite sides of the midvein with water (control) and a 1 μg/mL solution of cryptogein, an elicitor of defense responses in tobacco. Twelve hours later, 2.5 cm diameter leaf discs were cut from the infiltrated areas, homogenized with a mortar and pestle in GUS assay buffer, and protein extracts were assayed for GUS activity.

Figure 7B:
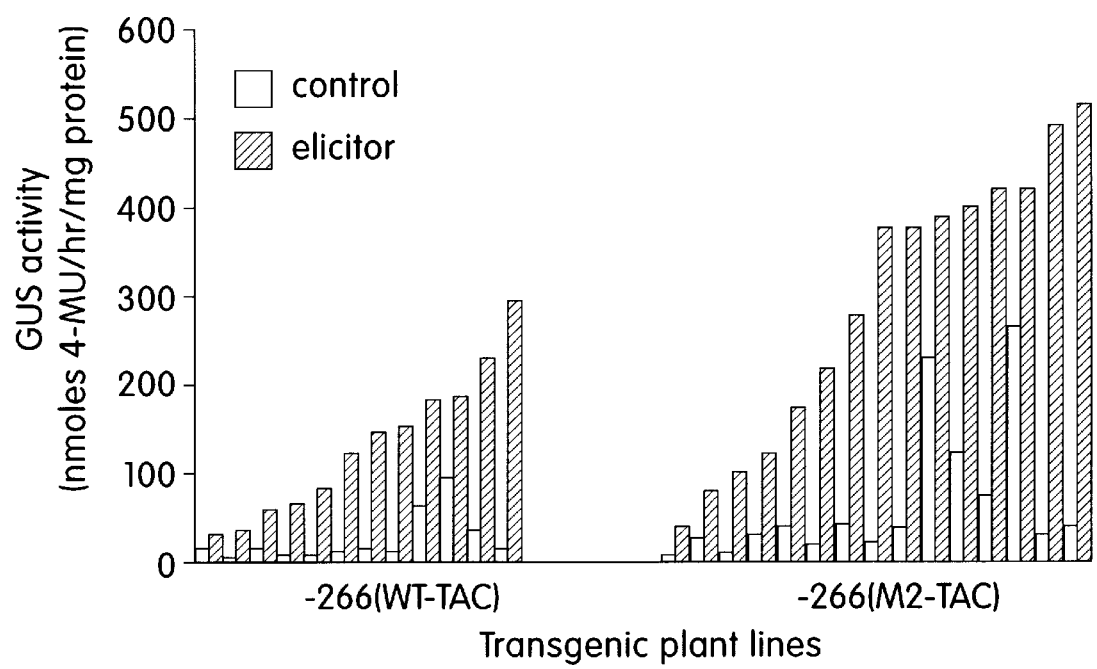
FIG. 7B is a graph showing the comparison of GUS activity in transgenic plants containing the wild-type TAC-box element (WT-TAC-Box) and the mutated TAC-box element (M2-TAC-Box) that were treated with elicitin. Tobacco plants were transformed with the GUS gene under the control of EAS4–266 to+73 region containing either the wild type or mutated TAC box. Leaves of F1 progeny were infiltrated with water or the elicitor cryptogein (1 μg/ml), protein was extracted from the infiltrated areas, and assayed for GUS activity. Each pair of bars (control and elicitor) represents an independent transgenic line. The height of each bar represents the mean value from at least 3 plants.

As shown in Table II and FIG. 7B, the leaves of plant lines transformed with the wild-type promoter contained a minimal amount of GUS activity when infiltrated with water, and approximately eleven-fold higher levels after elicitor treatment. Plant lines containing the mutated promoter upstream of the GUS gene showed a similar expression pattern, except that the absolute activity levels were two to three-fold higher than in transgenic plants containing the wild-type promoter. This increase in GUS activity was noted both in response to the control and elicitor treatments. These results indicated that, in the context of the truncated promoter, that the TAC-box element functions to suppress gene expression.

TABLE II

|  | GUS activity (nmoles/hr/mg) | |
| --- | --- | --- |
|  | median | mean ± s.d. |
| −266 (WT-TAC) control | 13 | 23 ± 26 |
| elicitor | 144 | 140 ± 83 |
| −266 (m2-tac) control | 37 | 64 ± 76 |
| elicitor | 376 | 299 ± 156 |

The experiments described above were carried out using the following techniques.

Oligonucleotides and Probes

Oligonucleotides were synthesized according to standard methods and are designated by position (number) and cod- Oligonucleotide primers were end-labelled with γ-$^{32}$P-ATP and radiolabelled DNA fragments were synthesized by standard polymerase chain reaction (PCR) protocols using the end-labelled primers as follows. Primer labeling reactions contained 25 pmole oligonucleotide, 1 μL 10×T4 kinase buffer (0.5 M Tris-HCl pH 7.6, 0.1 M MgCl$_2$, 50 mM DTT, 1 mM spermidine HCl, 1 mM EDTA), 25 μCi γ-$^{32}$P-ATP (3000 Ci/mmole), and 10 units of T4 kinase in a total volume of ten microliters. After incubation for thirty minutes at 37° C., the following components were added for the PCR reaction: 5 μL dNTPs (2.5 mM), 5 μL 10×kinase-PCR transition buffer (20 mM Tris pH 9.5, 0.5 M KCl, 0.1% Tween-20, 0.1% gelatin, 0.1% Nonidet P-40), one to ten nanograms template DNA (EAS4 promoter cloned in pBluescript), one unit Taq Polymerase (Gibco-BRL), fifty pmole second oligonucleotide (unlabelled), and water to a final volume of fifty microliters. Thermal cycling was performed with an annealing temperature of 50° C. for thirty-two cycles. PCR products were resolved on non-denaturing 12% (80:1) polyacrylamide gels, which were then exposed to Kodak X-Omat AR film for thirty seconds to two minutes to visualize the position of the probe in the gel. The radiolabelled fragment was excised from the gel, embedded in one percent agarose, and the radiolabelled fragment was then electrophoresed onto DE-81 paper (Whatman) or NA-45 membrane filters (Schleicher and Schuell). Next, the radiolabelled probe was eluted from the paper or membrane in elution solution (20 mM Tris pH 8.0, 2 mM EDTA, 1.5 M NaCl) for two hours at 60° C. and precipitated with two volumes ninety-five percent ethanol.

Extract Preparations

Tobacco cell suspension cultures were treated with elicitor (0.1 μg/mL cellulase) as described by Vogeli and Chappell (*Plant Physiol.* 94:1860–1866, 1990) and nuclei from these cultures were isolated as described by Watson and Thompson (*Meth. Enzymol.* 118:57–75, 1986) and extracted according to Dignam et al. (*Nucl. Acids Res.* 11:1475, 1983). Extracts from which TBBF was purified were prepared using a bead beater as described by Arias et al. (*Plant Cell* 5:485–496, 1994). Protein was determined by the Bradford method using Bio-Rad protein assay dye (Bio-Rad).

Whole cell extracts were prepared by a modification of the procedure described by Arias et al. (*Plant Cell*

5:485–496, 1994) as follows. Approximately 300 milliliters of two-day-old tobacco cell suspension culture were filtered on a wide pore (~0.5 mm) nylon mesh, the cells were washed with 200 milliliters of ice-cold water, weighed (approximately seventy-five to one hundred grams), and transferred to a chilled mortar. Approximately three grams of polyvinylpolypyrrolidone (PVPP) were sprinkled onto the cells, and the cells were then ground with a pestle. A small amount (~10 mL) of cold homogenization buffer was added to the cells and grinding was resumed. Homogenization buffer contained 0.2 M Tris, 0.39 M $(NH_4)_2SO_4$, 10 mM $MgSO_4$, 20% glycerol, 2 mM EDTA, 5 mM EGTA, and 2.5% dextran sulfate and was adjusted to pH 7.9 with glacial acetic acid. Immediately before use, 5 mM DTT, 1 mM PMSF, 2.5 µg/mL antipain, 0.35 µg/mL bestatin, and 0.4 µg/mL pepstatin A were added to the buffer. The ground cells were transferred to a large centrifuge bottle, along with 190 milliliters of cold homogenization buffer that was used to rinse the mortar and pestle, and fifteen drops of octanol were added to prevent foaming during homogenization. Homogenization was performed using a polytron at setting eight, three times for one minute, with chilling on ice between homogenizations. The homogenate was then filtered through wide pore nylon mesh as described above, and the filtrate was centrifuged at 10K (Sorvall SS34) for seven minutes. The supernatant was brought to 0.9 M $(NH_4)_2SO_4$ by the dropwise addition of 4 M $(NH_4)_2SO_4$ (pH 7.0) over thirty to sixty minutes. After stirring for thirty minutes, the extract was centrifuged at 15K in (Sorvall SS34) for thirty minutes, and the supernatant was decanted into a chilled beaker. Solid $(NH_4)_2SO_4$ (0.35 µ/mL homogenate) and 1 M KOH (10 µL/g $(NH_4)_2SO_4$) were slowly added over one hour while stirring, the homogenate was stirred for an additional thirty minutes, and then centrifuged at 15K (Sorvall SS34) for forty-five minutes. The protein pellet was resuspended (at a ratio of forty-five microliters to one gram of cells)in whole cell extract dialysis buffer (50 mM HEPES-KOH pH 7.9, 10 mM EGTA, 10 mM $MgSO_4$, 20% glycerol, 5 mM DTT, 0.5 mM PMSF) containing 4 µl/mL pepstatin A, 5 µ/mL leupeptin, 25 µ/mL antipain, and 35 µ/mL bestatin, and then dialyzed overnight against two changes of dialysis buffer.

Electrophoretic Mobility Shift Assays (EMSA)

Electrophoretic mobility shift assays (EMSA) contained 10 mM Tris (pH 7.9), 80 mM NaCl, 1 mM EDTA, 1 mM DTT, 5% glycerol, and five to twenty-five fmole of probe (10,000–50,000 dpm) in a total volume of ten microliters. The amount of protein and non-specific competitor DNA is indicated in the legend to appropriate figures. Samples were incubated for five to ten minutes at room temperature prior to loading on 12% acrylamide:bis (80:1) non-denaturing gels. The gels were run in 0.5×TBE buffer at 4° C.

Footprinting

Methylation interference experiments were performed using nuclear extracts as described by Baldwin (In: Ausubel et al, Current Protocols In Molecular Biology, John Wiley & Sons, New York, 1994).

DNase I footprinting using crude nuclear extracts used an approach similar to that for methylation interference. $MgCl_2$ (to 5 mM) and two micrograms DNaseI were added to fifty microliters of binding assay buffer, the reaction was incubated at room temperature for two minutes, and stopped by the addition of two microliters of 0.5 M EDTA. Bound and free DNA were separated by EMSA, isolated as above, and run on a 6% polyacrylamide sequencing gel. Quantitative footprinting analysis using purified TBBF was accomplished using the procedure of Brenowitz et al. (In: Short Protocols in Molecular Biology, Ausubel et al., eds., John Wiley & Sons, New York, 1992).

Site-directed Mutagenesis

Site-directed mutagenesis was performed according to the method of Kunkel et al. (*Meth. Enzymol.* 154:367, 1987). The mutagenized oligonucleotide was designed such that successfully mutated plasmids would lose the ScaI restriction enzyme recognition site (5' AGTACT 3') within the TAC box.

Purification of TAC-Box Binding Factor

DNA affinity chromatography: TAC box DNA-Sepharose was prepared essentially as described by Kadonaga and Tjian (*Proc. Natl. Acad. Sci.* 83:5889–5893, 1986). Oligonucleotides (dsTAC and dsTACn) were gel purified, annealed, ligated into multimers, and coupled to five milliliters (bed volume) of cyanogen bromide-activated sepharose (Sigma). The resulting affinity matrix contained approximately 400 µg DNA/5 mL sepharose.

Crude whole cell extracts containing 50–200 milligrams of protein were diluted with cold ZNG buffer and incubated for thirty minutes on ice with 0.3–0.5 milligrams of "fish sperm" DNA (Amersham) per milligram of protein. Buffer ZNG (25 mM HEPES-KOH pH 7.8, 12.5 mM $MgCl_2$, 1 mM DTT, 0.1% Nonidet P-40) is identical to Z buffer described by Kadonaga and Tjian (*Proc. Natl. Acad. Sci* 83:5889–5893, 1986), except that glycerol was omitted to accelerate the chromatography and ultrafiltration steps. The protein-fish sperm DNA mixture was passed over the TAC-box sepharose column and the flow throughs (designated FT1 and FT2) were collected as a single fraction. The column was then washed with twenty-five milliliters of ZNG buffer supplemented with 0.1 M KCl (low salt wash) followed by a 25 ML high salt wash with ZNG buffer containing 0.5 M KCl. All fractions were collected and assayed for DNA binding activity. This procedure was repeated until the majority of the binding activity was removed from the crude whole cell extract. Fractions demonstrating DNA binding activity in EMSA were combined, dialyzed against ZNG buffer, and concentrated by ultrafiltration.

Fast Protein Liquid Chromatography (FPLC): Combined fractions having DNA-binding activity that was obtained from DNA-affinity chromatography (above) were loaded onto a Mono-S column (Pharmacia) and eluted with a gradient of increasing ionic strength. Buffer A was identical to ZNG buffer; B buffer also contained 0.75 M KCl. Proteins were eluted at a flow rate of 0.5 mL/min using the following gradient: four minutes 0% B; forty minutes 0–33% B; twenty minutes 33–100% B; four minutes 100% B. One milliliter fractions were collected, and aliquots were diluted ten-fold prior to EMSA analysis. Fractions that demonstrated DNA activity in EMSA were combined, dialyzed against ZNG buffer, and concentrated by ultrafiltration. Proteins from these fractions were resolved by SDS-PAGE (Laemmli, *Nature* 227:680–685, 1970) using Duracryl high tensile strength acrylamide (Millipore) and stained with Silver Stain Plus (Bio-Rad).

Transgenic Plants and β-Glucuronidase (GUS) Assays

Transgenic tobacco plants containing chimeric gene fusions consisting of the EAS4 5'-untranslated region and 266 nucleotides upstream of the EAS4 transcription start site, that included either the wild-type (5' CAACTCTA-CAGTACTCCC 3'; SEQ ID NO: 19) or mutated TAC-box (5' CAACTCTAGTGTACTCCC 3'; SEQ ID NO: 20), were generated according to standard methods, e.g., those methods described in Chappell et al. (Transcriptional Control Sequences and Uses Thereof, U.S. Ser. Nos. 08/443,639, 08/471,983, and 08/577,483, filed May 18, 1995, Jun. 6, 1995, and Dec. 22, 1995, respectively) and Chappell et al. (WO97/012076).

Use

The nucleotide silencing elements and their binding factors described herein are useful for a variety of agricultural purposes known to those of skill in the art. The elements and binding factors described herein provided a means for negatively regulating the level of gene expression of a gene product. For example, an isoprenoid synthase gene silencing element (e.g., the TAC-box element) may be cloned into any promoter region as a means to decrease or inhibit plant gene expression. Silencing elements may be used to regulate gene transcription independent of their orientation and distance from a transcription start site. If desired, reiterated copies of such silencing elements may be used for transcriptional regulation of a given gene. Thus, the silencing elements of the invention may be positioned in the 5' or 3' transcriptional regulatory regions of a gene (e.g., the EAS4:ParA1 constructs that are described in Chappell et al., U.S. Ser. Nos. 08/443,639, 08/471,983, 08/577,483 and WO97/012076) that is to be transcribed. The effectiveness of a silencing element to reduce or eliminate gene expression may be monitored according to conventional methods (e.g., those methods described herein). If desired, genes encoding TBBF may also be introduced into a suitable host plant to regulate the expression of genes that are operably linked to a silencing element of the invention. Isolation and cloning of TBBFs useful in the invention is performed according to conventional methods well known in the art.

All publications and patents mentioned in this specification are herein incorporated by reference to the same extent as if each individual publication or patent was specifically and individually indicated to be incorporated by reference.

Other Embodiments

From the foregoing description, it will be apparent that variations and modifications may be made to the invention described herein to adopt it to various usages and conditions. Such embodiments are also within the scope of the following claims.

What is claimed is:

1. An isolated gene silencing regulatory element comprising 5' TACNNTAC 3' (nucleotides 2 to 9 of SEQ ID NO:1).

2. The isolated gene silencing regulatory element of claim 1, wherein said gene silencing regulatory element comprises 5' CTACAGTACT 3' (SEQ ID NO:2).

3. The isolated gene silencing regulatory element of claim 1, wherein said gene silencing regulatory element comprises 5' TCTACAGTACT 3' (SEQ ID NO:3).

4. The isolated gene silencing regulatory element of claim 1, wherein said gene silencing regulatory element comprises 5' ACTCTACAGTACTC 3' (SEQ ID NO:4).

5. The isolated gene silencing regulatory element of claim 1, wherein said gene silencing regulatory element is an isoprenoid synthase gene silencing regulatory element.

6. The isolated gene silencing regulatory element of claim 5, wherein said isoprenoid synthase is a sesquiterpene synthase.

7. The isolated gene silencing regulatory element of claim 6, wherein said sesquiterpene synthase is epi-5-aristolochene synthase.

8. The isolated gene silencing regulatory element of claim 1, wherein said gene silencing regulatory element is from a dicot.

9. The isolated gene silencing regulatory element of claim 8, wherein said dicot is a member of the Solanaceae.

10. The isolated gene silencing regulatory element of claim 9, wherein said dicot is a member of the genus Nicotiana.

11. The isolated gene silencing regulatory element of claim 1, wherein said gene silencing regulatory element is from a monocot.

12. The isolated gene silencing regulatory element of claim 1, wherein said gene silencing regulatory element is from a gymnosperm.

13. The isolated gene silencing regulatory element of claim 1, wherein said gene silencing regulatory element is from a conifer.

14. A vector comprising the gene silencing regulatory element of claim 1.

15. The vector of claim 14, wherein said gene silencing regulatory element is operably linked to a nucleic acid sequence, and wherein said gene silencing regulatory element decreases expression of said nucleic acid sequence in a cell transformed with said vector.

16. A transgenic plant comprising the isolated gene silencing regulatory element of claim 2 or the vector of claim 14 integrated into the genome of said plant.

17. A seed from the transgenic plant of claim 16.

18. A cell from the transgenic plant of claim 16.

19. A method of decreasing the transcription of a DNA sequence in a transgenic plant, said method comprising the steps of:

(a) transforming a plant cell with a DNA sequence which is operably linked to the gene silencing regulatory element of claim 1 to produce a transgenic plant cell; and (b) regenerating said transgenic plant from said transgenic plant cell; wherein transcription of said DNA sequence is decreased as compared to a transgenic plant transformed with said DNA sequence which is not operably linked to said gene silencing regulatory element.

* * * * *